(12) United States Patent
Scolan et al.

(10) Patent No.: US 10,656,091 B2
(45) Date of Patent: May 19, 2020

(54) OPTICAL SENSOR FOR DETECTING A CHEMICAL SPECIES

(71) Applicant: CSEM CENTRE SUISSE D'ELECTRONIQUE ET DE MICROTECHNIQUE SA-RECHERCHE ET DEVELOPPEMENT, Neuchatel (CH)

(72) Inventors: Emmanuel Scolan, Neuchatel (CH); Bernard Wenger, Chaumont (CH); Raphael Pugin, Colombier (CH)

(73) Assignee: CSEM CENTRE SUISSE D'ELECTRONIQUE ET DE MICROTECHNIQUE SA—RECHERCHE ET DEVELOPPEMENT, Neuchatel (CH)

( * ) Notice: Subject to any disclaimer, the term of this patent is extended or adjusted under 35 U.S.C. 154(b) by 0 days.

(21) Appl. No.: 15/384,340

(22) Filed: Dec. 20, 2016

(65) Prior Publication Data

US 2017/0176332 A1   Jun. 22, 2017

(30) Foreign Application Priority Data

Dec. 21, 2015  (EP) ..................... 15201731

(51) Int. Cl.
*G01N 21/64* (2006.01)
*B82Y 30/00* (2011.01)
(Continued)

(52) U.S. Cl.
CPC ............ *G01N 21/645* (2013.01); *B82Y 30/00* (2013.01); *G01N 21/6428* (2013.01);
(Continued)

(58) Field of Classification Search
None
See application file for complete search history.

(56) References Cited

U.S. PATENT DOCUMENTS 5,250,095 A   10/1993   Sigel, Jr. et al.
7,740,904 B2   6/2010   Shahriari
(Continued)

FOREIGN PATENT DOCUMENTS

WO   2006/119986 A1   11/2006
WO   2009/118271 A1   10/2009

OTHER PUBLICATIONS

Shengyang Tao et al: "Hierarchically Structured Nanocomposite Films as Highly Sensitive Chemosensory Materials for TNT Detection", Chemphyschem—A European Journal of Chemical Physics & Physicalchemistry, Wiley—V C H Verlag Gmbh & Co. KGAA, DE, vol. 7, No. 9, Sep. 11, 2006 (Year: 2006).*
(Continued)

*Primary Examiner* — Kathryn Wright
(74) *Attorney, Agent, or Firm* — Young & Thompson

(57) ABSTRACT

An optical sensor (1) for detecting a chemical species includes a substrate (3), a mesoporous matrix (5) disposed on the substrate, and a microporous matrix (7) disposed within the mesoporous matrix. The microporous matrix (7) includes an indicator dye (9) dispersed therein, the indicator dye (9) exhibiting changes in its optical properties in response to the presence of the chemical species. This arrangement significantly increases the amount of dye present, while allowing the medium to be analyzed greater access through the porous structure, thereby increasing the performance of the sensor.

15 Claims, 8 Drawing Sheets

(51) Int. Cl.
    *G01N 21/77*   (2006.01)
    *G01N 31/22*   (2006.01)
    *G01N 33/00*   (2006.01)
    G01N 21/78    (2006.01)
    G01N 21/80    (2006.01)

(52) U.S. Cl.
    CPC ............ *G01N 21/77* (2013.01); *G01N 31/22* (2013.01); *G01N 33/004* (2013.01); G01N 21/6408 (2013.01); G01N 21/78 (2013.01); G01N 21/783 (2013.01); G01N 21/80 (2013.01); G01N 31/221 (2013.01); G01N 31/223 (2013.01); G01N 2021/6432 (2013.01); G01N 2021/6434 (2013.01); G01N 2021/6439 (2013.01); G01N 2021/7726 (2013.01); G01N 2021/7786 (2013.01)

(56) References Cited

U.S. PATENT DOCUMENTS

| | | |
|---|---|---|
| 8,313,710 B2 | 11/2012 | Kane |
| 2003/0068827 A1 | 4/2003 | Morris et al. |
| 2004/0171094 A1 | 9/2004 | Klimant et al. |
| 2008/0199360 A1 | 8/2008 | Shahriari |
| 2010/0312483 A1* | 12/2010 | Peyser .................. G01N 33/52 702/19 |
| 2011/0024771 A1* | 2/2011 | Hajj-Hassan .......... B82Y 15/00 257/84 |

OTHER PUBLICATIONS

Extended European Search Report issued in Application No. 15 20 1731, dated Jun. 23, 2016.
Chu et al., "Highly Sensitive and Linear Optical Fiber Carbon Dioxide Sensor Based on Sol-Gel Matrix Doped with Silica Particles and HPTS", Sensors and Actuators B: Chemical: International Journal Devoted to Research and Development of Physical and Chemical Transducers, Dec. 4, 2009, pp. 205-210, vol. 143, No. 1.
Martinez-Ferrero et al., "Optical Properties of Hybrid Dendritic-Mesoporous Titania Nanocomposite Films", Chemistry—A European Journal, Jul. 30, 2008, pp. 7658-7669, vol. 14, No. 25.
Zhou et al., "Enhanced Photoluminescence of Oxygen Sensing Films through Doping with High Dielectric Constant Particles", Advanced Functional Materials, Oct. 4, 2007, pp. 3530-3537, vol. 17, No. 17.
Zhang et al., "Porous Ionic Liquids: Synthesis and Application", Chemical Science, May 22, 2015, pp. 3684-3691, vol. 6, No. 7.
Anonymous, "FluoroMax—Compact Steady State Spectrofluorometer, HORIBA Scientific—HORIBA", Apr. 12, 2015, Retrieved from the Internet:http://www.horiba.com/scientific/products/fluorescence-spectroscopy/steady-state/fluoromax/fluoromax-series-524/ (4 pages).
"Micropore in Catalysis", IUPAC Compendium of Chemical Terminology, Jun. 12, 2009, IUPAC.

\* cited by examiner

OPTICAL SENSOR FOR DETECTING A CHEMICAL SPECIES

TECHNICAL FIELD

The present invention relates to the field of optical sensors for detecting the presence of chemical substances, such as $O_2$ and $CO_2$, and also oxonium ($H_3O^+$) and/or hydroxide ions ($OH^-$).

STATE OF THE ART

Luminescent gas sensors for detection of oxygen or carbon dioxide have been introduced in the market during the last decade. The most successful products so far are oxygen sensors that have been commercialized by several companies. Compared to electrochemical sensors they are more stable and are available in cheap—and accurate—devices. Many suppliers of electrochemical oxygen sensors, such as Mettler-Toledo, Hamilton, Hach Lange, and YSI, are now providing an optical version. A few companies are also providing patches that can be inserted into bottles or packages in order to optically measure the amount of oxygen from outside of the container, through its transparent wall. Companies which commercialise such products are Ocean Optics, Polestar, Pyro-Science, Oxysense, and Presens.

The technology is typically based on the encapsulation of a luminescent dye (e.g. ruthenium complexes, metalloporphyrins) in an inert matrix. In the presence of oxygen, the excited state of the dye is non-radiatively deactivated leading to a decrease in the intensity and also in the lifetime of the luminescence. The matrix can be either a polymer resin or a metal oxide porous film obtained by sol-gel chemistry. Organically-modified silica (ormosil) is often used for the matrix due to its chemical compatibility and ease of processing.

A similar approach has been used for the detection of $CO_2$ or pH. Both luminescent and colorimetric (measurement of optical absorbance) measurement schemes have been proposed. For these analytes, the liquid medium must be in direct contact with the sensing chemical compounds.

Therefore porosity and accessibility to the luminophore have a crucial impact on the sensitivity and the reaction time. In the case of gaseous $CO_2$, the mechanism is based on a local change in pH upon reaction with a quaternary ammonium base selective for $CO_2$. This event is monitored with a pH indicator dye that can be luminescent or coloured. Only few solutions are commercially available, for example from Presens and Polestar, which both use a luminescent indicator.

In the patent literature, WO2009/118271, U.S. Pat. No. 7,740,904, US2008/0199360 and US2003/0068827 disclose indicator dyes entrapped in a sol-gel deposited matrix. The matrix is prepared from water crosslinked silicon alkoxides, thus leading to microporous silicate structures. US2004/0171094 discloses oxygen sensor dye enclosed within small polymer particles permeable to gases but not to water, with diameters between a few nm and a few µm. These dyes respond by changing colour in the visible spectrum or by changes in luminescence when stimulated by ultraviolet light in the presence of a substance to be detected. These changes in colour, or luminescence can be optically measured. If the response of the indicator dye is sufficiently smooth, such sensors can either be calibrated to indicate the concentration of a substance (e.g. $H^+/OH^-$ ions in a pH sensor, $CO_2$, $O_2$, organic and inorganic vapours, toxic agents, flammable agents and so on) by using a suitable calibration curve. If not, the sensors can be used in a binary detection role, i.e. indicating the presence or absence of substance above a predetermined threshold concentration.

However, these prior art sensors are restricted in their response time and/or the strength of their colour/fluorescent response due to limitations on the amount of dye which can be exposed to the chemical species of interest due to limited porosity of the substrates, and the need to keep the layers thin (typically 1 µm maximum) to ensure a reasonable response time and optical readout. On the other hand, the tight matrix around the sensitive dyes protects them from leaching and photodegradation.

Moreover, systems based on dyes encapsulated into meso- and macroporous matrices have also been reported.

U.S. Pat. No. 8,313,710 discloses porous polymer matrices with pore sizes ranging between 100 nm and 20 µm. The sensitive materials are covalently bonded into the porous matrix to prevent any release in the measured medium.

U.S. Pat. No. 5,250,095 reports a method to generate a porous glass at the surface of a glass optical fibre using a phase separation process. The average pore size is below 150 nm with a surface area greater than 50 $m^2$ per gram. This porous support hosts dyes to get colorimetric sensors of ammonia and humidity.

Finally WO2006/119986 describes a gas-sensor comprising a solid support, and a pseudo-boehmite mesoporous membrane. The membrane presents an average pore diameter of the pores in the 1 to 50 nanometers range, preferably in the 5 to 30 nanometers range. The membrane is charged with gas selective compounds which, along with additives, are responsible for the spectral change upon interaction with a specific gas. The gas selective compounds are accordingly directly adsorbed on the mesoporous membrane surface, including on the inner surface of the membrane, within the mesopores.

The sensitivity of the gas-selective compound in the mesoporous membrane matrix strongly depends on the pore size and on the amounts of mesopores in the membrane matrix or the total pore volume. To keep response time fast and within convenient range, limited pore size and low thickness is required.

The meso- and macroporous matrices based systems described in these patents provide large accessible surface areas and pore sizes that make the optical signal intensity higher and the response time lower respectively than those of microporous matrices. However, they can only be used for gas detection, unless a specific approach is used to prevent the sensitive compounds from leaching, such as the covalent bonding reported in U.S. Pat. No. 8,313,710. Moreover, the transparency of the meso-/macroporous layers is reduced compared to that of microporous matrices, due to their higher thicknesses and the increased probability that they contain scattering objects. Additionally, since the sensitive compounds are not entrapped in a tight environment in meso- and macroporous matrices, they degrade very fast, generating signal and sensitivity drift of the sensor.

An aim of the present invention is thus to overcome first the above-mentioned disadvantages of optical sensors based either on microporous or meso- and macroporous sensitive layers embedding photosensitive dyes. In particular, an aim of the invention is to provide an optical sensor for detecting chemical species with rapid response times and improved intensity of colour and/or fluorescent response. Another aim of the invention is to provide an optical sensor for detecting chemical species which can be used to detect such species in gas and liquids, in particular in aqueous solutions, while protecting the dyes embedded in the sensor from leaching and photodegradation.

DISCLOSURE OF THE INVENTION

More precisely, the object of the invention is resolved by an optical sensor for detecting a chemical species, such as oxygen, carbon dioxide, $H^+$ or $OH^-$ ions (i.e. for sensing pH), said sensor comprising a substrate (such as metal, plastic, glass, ceramic, or similar), a mesoporous matrix disposed on the substrate, and a microporous matrix disposed within the mesoporous matrix.

The microporous matrix comprises an indicator dye dispersed therein, said indicator dye exhibiting changes in its optical properties, i.e. colour (hue and/or intensity), luminescence (intensity and/or lifetime) or similar, in response to the presence of said chemical species. The optical sensor is thus a luminescent and/or colorimetric sensor depending on the dye used.

The use of a hierarchical porosity, i.e. a dye-containing microporous (typically defined as comprising pores of 2 nm or less) matrix embedded within a mesoporous (typically defined as comprising pores of between 2 nm and 50 nm, preferably between 10-50 nm) matrix, increases the performance of the sensors.

The inclusion of the dye in the microporous matrix, as opposed to the solution of WO2006/119986, and the additional inclusion of the microporous matrix within the mesoporous matrix provides a thin layer formed inside the mesoporous network. Such optical sensing layer of multiple hierarchical matrices exhibits controlled pores sizes over the thickness of the mesoporous matrix. Thereby, the pores remain accessible for the medium to be analysed (gas or liquid) increasing the performance of the sensors and ensuring low response time and strong optical response due to the larger amount of indicator dye.

The mesoporous matrix increases the surface area available for deposition of the microporous material, and thereby increases the amount of dye present (and hence the colour or luminescence intensity). Furthermore, the mesoporosity permits circulation of gas or liquid which may contain the chemical species of interest, giving a low response time. The microporous matrix permits the entrapment of sensitive materials in very thin layers of microporous matrix material. The microporous matrix therefore provides with a higher resistance to dye leaching, to fading (due to dye oxidative degradation), and an improved sensitivity, mechanical resistance, and transparency.

They are several advantages to the inclusion of a microporous matrix within a mesoporous one to provide a hierarchical sensing device as proposed by the invention. It reinforces the mechanical resistance of the mesoporous network by enlarging the nanoparticle boundaries. The microporous matrix further increases the resistance to mechanical stress and reduced cracking, better adhesion and resistance to hydrolysis. The hierarchical optical sensing layer shows an important gain in signal stability compared to a mesoporous layer and the normalized signal varies linearly with the normalized pressure.

Another advantage of the invention is that the optical sensor is for detecting chemical species in gas and also in liquids, in particular in aqueous solutions, while preventing the dyes embedded in the sensor from leaching and photodegradation.

Taking all these parameters into account, the response time of a hierarchical optical sensing layer has been improved over a mesoporous layer, for example the withdrawal of $O_2$ in the surrounding gas environment lasts several minutes from a mesoporous layer and less than 1 ms in the hierarchical optical sensing layer according to the invention. The sensitivity performance of the hierarchical system remains stable for several weeks in different aqueous solutions.

Typically, the chemical species to be detected is oxygen, carbon dioxide, or $H^+$ ions and/or $OH^-$ ions, these latter being detected in the case of a pH sensor. Accordingly, the sensitive dye within the microporous matrix may comprise at least one of the following dye molecules: bromophenol blue, alizarin, methyl red, phenol red, m-cresol purple, p-xylenol blue, naphtol blue black, fluorescein, eosin, calmagite, naphtholphtalein, ruthenium complexes, porphyrines, and pyrenes.

Advantageously, the mesoporous matrix is formed as a layer having a thickness in the range of 1-50 µm, preferably 5-40 µm, giving a good compromise between amount of dye present and response time.

Advantageously, the microporous matrix within the mesoporous matrix is formed as a layer having a thickness of less than 100 nm, preferably less than 20 nm to prevent pores from blocking.

Furthermore, the optical sensor may be incorporated into a sensor system comprising an optical sensor as defined above, a light source (such as a lamp, an LED, a laser or similar) arranged to illuminate said microporous matrix and said indicator dye, and a detector arranged to receive light emanating from said indicator dye. "Emanating" includes not only reflected light, but also light emitted by the dye. A sensor system that can be calibrated is thus proposed.

The aim of the invention is also attained by a method of producing an optical sensor. This method comprises the steps of:
  providing a substrate (such as metal, plastic, glass, ceramic, or similar);
  depositing a mesoporous matrix on the substrate;
  depositing a microporous matrix within the mesoporous matrix, the microporous matrix comprising an indicator dye dispersed therein, said indicator dye exhibiting changes in its optical properties in response to the presence of said chemical species.

As mentioned above and repeated here, a hierarchical porosity, i.e. dye-containing microporous (typically defined as comprising pores of 2 nm or less) matrix deposited upon a mesoporous (typically defined as comprising pores of between 2 nm and 50 nm, preferably between 10-50 nm) matrix, increases the performance of the sensors by increasing the dye load of the layer while keeping the entrapment microporous layer very thin. Furthermore, the mesoporosity permits circulation of gas or liquid which may contain the chemical species of interest, giving a quick response time.

Typically, the chemical species to be detected is oxygen, carbon dioxide, or $H^+$ ions and/or $OH^-$ ions, these latter being detected in the case of a pH sensor.

Advantageously, the mesoporous matrix is deposited as a layer having a thickness in the range of 1-50 µm, preferably 5-30 µm, giving a good compromise between amount of dye present and response time.

Advantageously, the microporous matrix is deposited as a layer having a thickness of less than 100 nm, preferably less than 20 nm to prevent pores from blocking.

BRIEF DESCRIPTION OF THE DRAWINGS

Further details of the invention will appear more clearly upon reading the following description in reference to the annexed figures, which illustrate.

EMBODIMENT OF THE INVENTION

Figure 1:
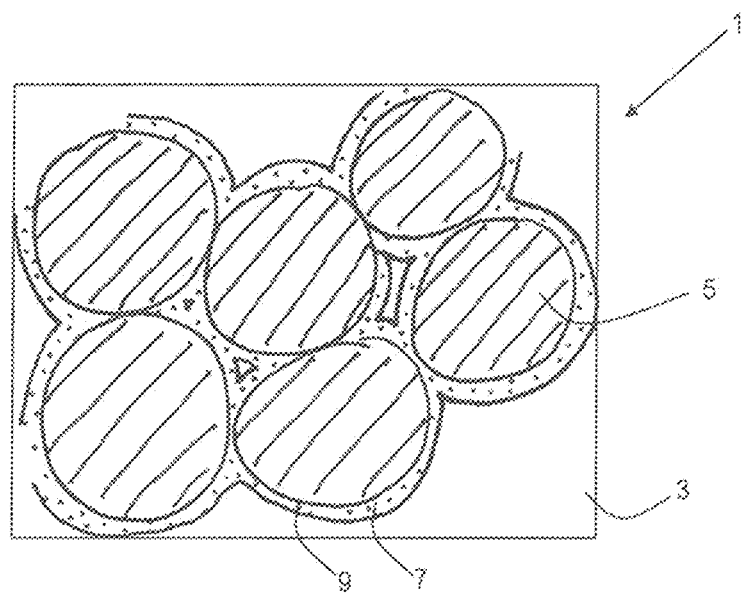
FIG. 1—a schematic close-up view of the structure of an optical sensing layer according to the invention.

FIG. 1 shows schematically a close-up view of the structure of an optical sensing layer 1 according to the invention. Sensing layer 1 comprises a substrate 3, which may be glass, plastic, ceramic, metal or any other convenient material, upon which is deposited a mesoporous matrix 5. A mesoporous material is defined as a material with pore diameter between 2 and 50 nm between individual, substantially non-porous particles of material. A typical mesoporous matrix 5 for this application is formed by metal oxide layers obtained by deposition of nanoparticles from solution, and is deposited on the substrate 3, which is typically flat although this does not have to be the case. The thickness of these layers is typically comprised between about 1 and about 50 μm, and the size and density of the mesoporous particles are chosen to preferably achieve a pore size in the range of 10-50 nm. The mesoporous matrix 5 thus provides a vastly-increased surface area compared to a flat surface, and is extremely porous due to the network of percolation passages formed by the interconnecting pores around the individual particles making up the mesoporous matrix 5. Hence, gases, liquids, ions in solution etc. can enter and exit the pores, and can intimately contact the indicator dye (see below).

As examples of forming the mesoporous matrix 5 on the substrate 3, thin films of mesoporous inorganic materials can be obtained by deposition of nanoparticles dispersions of various metal oxides like silica, alumina, titania, zirconia, etc. With adequate formulations, such layers show good transparency (transmission >80%), mechanical and chemical stability. In addition they can be coated on various substrates including large area flexible polymer sheets. For example, this approach was used successfully for commercial high-resolution ink-jet supports—as a result, such deposition technology is known and does not need to be further explained. Several coating processes are suitable for the formation of these layers like spin-coating, bar-coating, slot-die coating or curtain coating.

Deposited upon the mesoporous matrix 5 is a microporous matrix 7, encapsulating an indicator dye 9. A hierarchical porosity structure is thus provided, with the microporous matrix 7 within the mesoporous matrix 5.

Such an indicator dye 9 changes its optical properties (absorption, luminescence) in the presence of a chemical species to be detected, such as oxygen, carbon dioxide, $H^+$ ions, and so on. Such indicator dyes as such are well-known and do not need to be further described, although specific examples are given below. The changes in optical properties of the indicator dye 9 can take place in the infrared, visible, and/or ultraviolet ranges, in response to impinging infrared, visible or ultraviolet light. These changes may be simple colour changes (i.e. changes in absorbed/reflected wavelength and/or intensity), or may be changes in intensity, lifetime wavelength of luminescent response.

To prevent leaching into the environment (i.e. the surrounding gas or liquid), the dye indicators are typically immobilized by physical entrapment in a microporous inorganic matrix obtained by sol-gel chemistry (pore diameter <2 nm).

In the prior art, dye functionalised microporous material has been used directly as a sensing film when deposited on a flat substrates, for example polymer sheets or glass. However due to the limited pore size of the microporous matrix 7, only thin layers can be used in order to keep the response time within a convenient range. Typically, the thickness of such layers must be kept below 1 μm. An example of application can be found in Schyrr et al. [Sens. Actuat. B, 194 (2014) 238-248] describing optical fibers modified with pH-sensitive coatings for on-body monitoring. As a consequence of this thickness limit, the amount of entrapped indicator dye 9 molecules and consequently the optical signal intensity are limited.

According to the invention, the optical sensing layer 1 comprises a mesoporous matrix 5 deposited on a substrate as described above and further the microporous matrix 7 which is deposited within the mesoporous matrix 5. The inclusion of the microporous matrix 7 within the mesoporous matrix 5 provides a thin conformal layer formed inside the mesoporous network, thereby forming a hierarchical optical sensing layer, i.e. an optical sensing layer of multiple matrices comprising varied but controlled pores sizes over the thickness of the mesoporous matrix. By controlling the amount of microporous matrix 7 material deposited, the pores of that microporous matrix 7 remain accessible for the medium to be analyzed (gas or liquid) thereby ensuring low response time of the optical sensing layer 1 of the invention and a strong colour response due to the larger amount of indicator dye 9 present in the hierarchical matrices system resulting from sensing layer 1.

Figure 2:
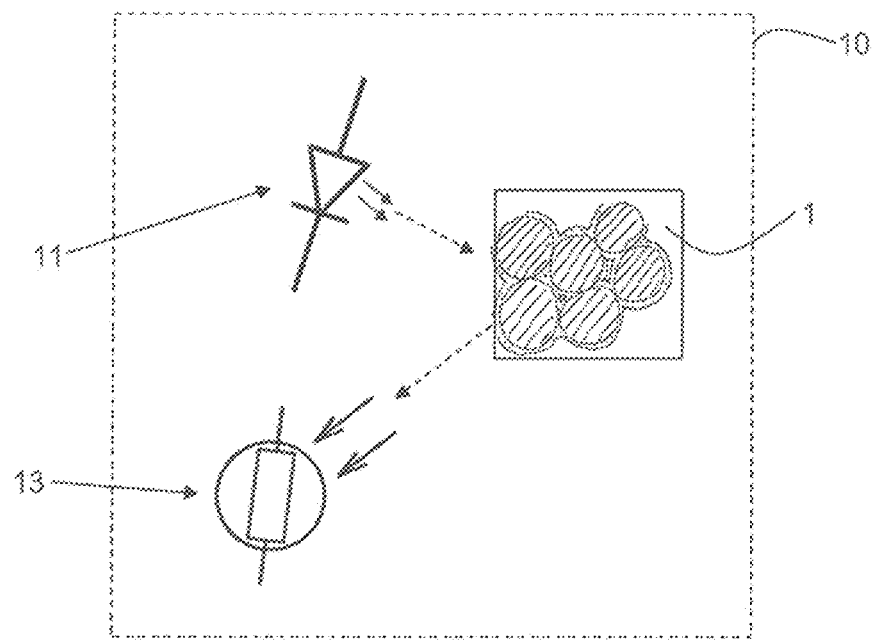
FIG. 2—a schematic view of an optical sensor system incorporating an optical sensor according to the invention.

The above-mentioned changes in optical properties of the indicator dye 9 are typically measured with a suitable optical sensor system 10, as illustrated schematically in FIG. 2. Such a system 10 comprises an optical sensing layer 1 according to the invention, a light source 11 (a light bulb, an LED, a laser or similar) arranged to shine light (infrared, visible, ultraviolet or any combination thereof, either broadband or narrow band) onto the optical sensing layer 1 so as to excite the dye 9. The system 10 further comprises a light detector 13, arranged to receive light reflected or emitted (i.e. generated due to luminescent effects) from optical sensing layer 1 in response to light from the light source 11 impinging thereupon, in one or more of the infrared, visible or ultraviolet ranges. Advantageously, shielding (not illustrated) may be provided to prevent ambient light from falling on the optical sensing layer 1 and/or on the light detector 13.

However, in its most simple form, use of such an optical sensor system 10 is not necessary if the changes in optical properties take place in the visible spectrum under ambient light, or as luminescent effects visible using a conventional UV source, and can thus be perceived by a person, e.g. in the case of an indicator dye changing from one colour to another (e.g. red to blue), or from colourless to coloured, or fluorescing or not when exposed to a UV lamp. Such a simplified arrangement cannot provide objective calibrated results, although manual comparison with a calibrated colour chart is possible.

Having now outlined the principle of the invention, several concretisations of the microporous matrix 7, indicator dye 9 and so on, are contained in the following.

As mentioned above, the microporous matrix 7 is typically prepared using sol-gel chemistry. Typically, the sol-gel formulation used to encapsulate the optically active agents, i.e. the indicator dye 9, is composed of a solvent, a mixture of silanes and acidified water. The solvent may be chosen among polar solvents able to dissolve the different components. Examples of such solvents include: short chain alcohols, tetrahydrofuran (THF), dimethyl formamide (DMF), and dimethyl sulfoxide (DMSO). The water is typically acidified with inorganic acids, such as HCl, $H_2SO_4$ or $H_3PO_4$. The pH value of the acidified water typically ranges from 0 to 4 and ideally from 1 to 3. The water amount is determined as a molar ratio with all silanes. This molar ratio H=[Water]/[silanes] ranges typically from 1 to 10 and preferably between 3 to 6.

Finally, the silanes are typically selected among:
Bulk forming silanes $SiX_4$.
Surface modifying silanes $RSiX_3$.
Linear modifiers $R1R2SiX_2$.
Bridging silanes $X_3Si-R-SiX_3$:$R1X_2Si-R2-SiX_2R1$, $R12XSi-R2-SiXR12$, where X stands for a hydrolysable group, typically alkoxy, chloro group; R, R1, R2 are organic groups linked to the Si atom through a C—Si bond; typically, alkyl, vinyl, phenyl, amino-alkyl, perfluoro-alkyl, epoxy-alkyl, thio-alkyl, hydroxyl-alkyl, cyanato-alkyl, thiocyanato-alkyl, polyethyleneoxy-alkyl, pyridyl-alkyl groups.

The molar ratio S=[Solvent]/[silanes] typically ranges from 0 to 100 and ideally from 0 to 60. Finally, the sensitive agent, typically a dye molecule, is dissolved in a concentration range of typically $10^{-5}$ to 1 M and preferably from $10^{-3}$ to $10^{-1}$ M. Typical dyes are bromophenol blue, alizarin, methyl red, phenol red, m-cresol purple, p-xylenol blue, naphtol blue black, fluorescein, eosin, calmagite, naphtolphtalein, ruthenium complexes, porphyrines, pyrenes, and luminescent particles, including semi-conducting quantum dots (e.g. CdSe, InP, ZnS), metallic nanoparticles (e.g. Au, Ag, Cu, Ni), and metal oxide nanoparticles (e.g. ZnO, rare earth doped $YVO_4$).

Example of Formulation for Oxygen-Sensing Films

An example of producing a sensor for detecting oxygen as a chemical species of interest follows hereunder.

In a typical experiment 0.71 mL of methyltriethoxysilane (MTES) and 0.68 mL of (3,3,3-trifluoropropyl)trimethoxysilane (FTP-TMOS) are added to 2 mL of ethanol. Then 0.5 mL of HCl acidified water (pH=1) is added dropwise. Finally, 12.5 mg of $Ru(dpp)_3$ dissolved in 0.6 mL of ethanol are added to the mixture, which is stirred overnight. The $Ru(dpp)_3$ complex is the indicator dye 9 which phosphorescence is quenched in the presence of the chemical species of interest, namely oxygen.

The resulting sol is then spread over a mesoporous matrix 5, comprising silica or alumina. The thus functionalized mesoporous matrix 5 is dried overnight in room conditions, the sol drying on the surface of mesoporous matrix 5 to form microporous matrix 7 comprising the ruthenium-complex indicator dye 9. The microporous matrix 7 is then dipped in a pH=9 solution, to complete siloxy group crosslinking.

Figure 3:
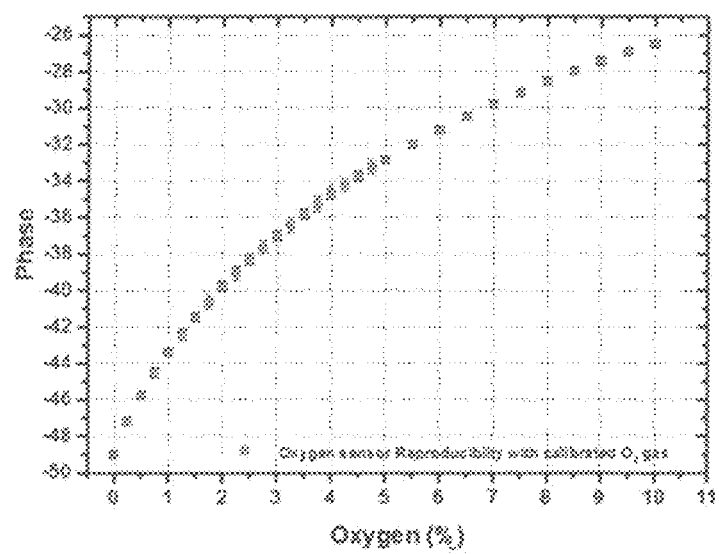
FIG. 3—a calibration curve for an oxygen sensor incorporating an optical sensing layer according to the invention.

FIG. 3 illustrates a calibration curve for the resulting sensor system 10 incorporating an optical sensing layer 1 provided with the mesoporous matrix 5, microporous matrix 7 and indicator dye 9 as described in the preceding paragraphs. The horizontal axis represents the percentage of oxygen in the gas contacting the optical sensing layer 1, and the vertical axis represents the phase shift of the light received by the light detector 13 when the sensing layer 1 is excited with a blue LED whose intensity is modulated at 25 kHz.

Figure 4:
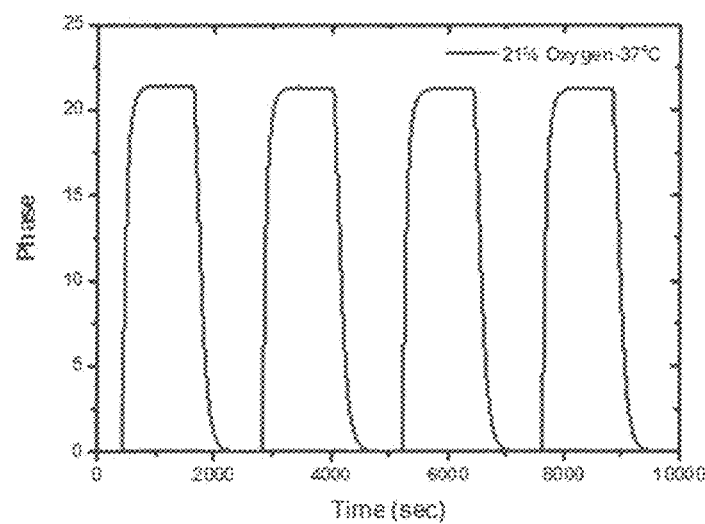
FIGS. 4, 5, and 6—graphs of experimental results measured using an oxygen sensor incorporating an optical sensing layer according to the invention.
Figure 5:
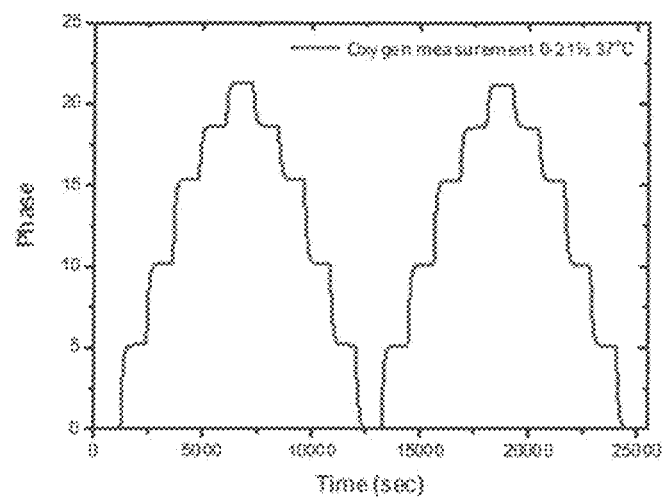
Figure 6:
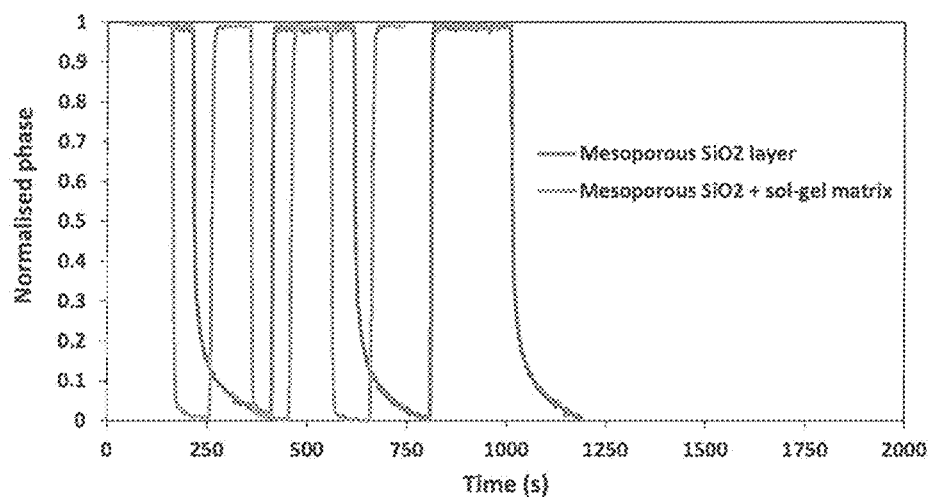

FIGS. 4, 5, and 6 illustrate experimental results for detecting oxygen. FIG. 4 illustrates the results obtained by exposing the sensor system 10 to pure nitrogen and atmospheric air (21% oxygen) alternately. FIG. 5 illustrates the results obtained with step changes of oxygen concentration using calibrated gases in the following sequence of concentrations: 0-5-10-15-21-15-10-5-0-5-10-15-21-15-10-5-0%. The precision of measurement is extremely good and the repeatability is excellent. FIG. 6 compares the difference of response time between two $Ru(dpp)_3$ functionalised mesoporous $SiO_2$ layers. The first one was functionalised with an ethanolic solution of $Ru(dpp)_3$ ('mesoporous $SiO_2$ layer'). The second is a hierarchical optical sensing layer according to the invention: the mesoporous $SiO_2$ layer was functionalised with a HCl acidified MTES based sol containing the $Ru(dpp)_3$ dye. The hierarchical sensing layer exhibit lower response times than the mesoporous layer, specifically by reducing the $O_2$ exposure.

The improvement of the response time of a hierarchical optical sensing layer according to the invention over a mesoporous layer as known from the prior art is shown in FIG. 6. The signal varies with $O_2$, switching between pure $N_2$ and the air. The withdrawal of $O_2$ lasts several minutes from a mesoporous layer and less than 1 s in the hierarchical optical sensing layer according to the invention. In addition in the hierarchical sensing layer of the invention, this microporous matrix reinforces the mechanical resistance of the mesoporous network by enlarging the nanoparticle boundaries.

The hierarchical optical sensing layer of the invention also shows an important gain in signal stability compared to that of the mesoporous films from the prior art with soluble dyes in the measured solvent (e.g. water soluble dyes for measurement of pH in an aqueous solution).

Figure 7:
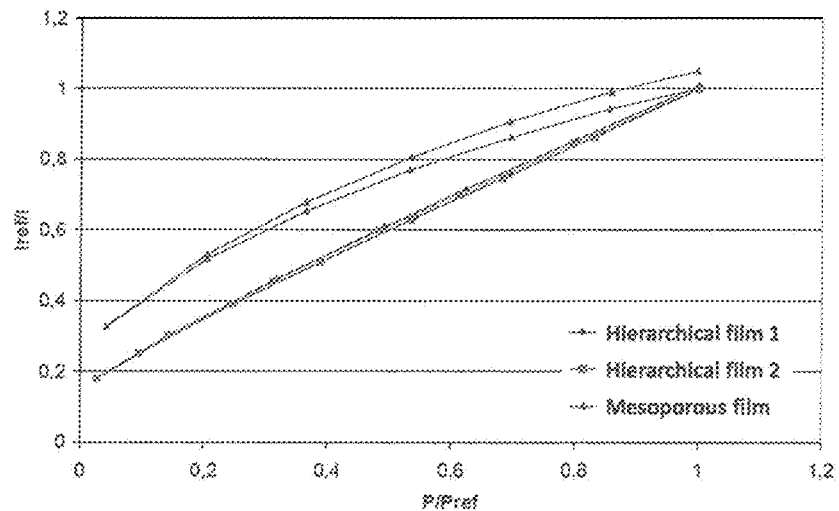
FIG. 7—a calibration curve for oxygen sensing using an oxygen sensor incorporating two different optical sensing layers according to the invention (Hierarchical film 1 and 2) and an optical sensing layer based on a purely mesoporous film.

Moreover, a signal drift from mesoporous films is observed under irradiation, while the signal from hierarchical sensing layers according to the invention remains stable (see FIG. 7). In addition, the calibration of the signal is improved with a hierarchical optical sensing layer according to the invention compared to a mesoporous layer only as taught in the prior art (FIG. 7). The normalised signal of a hierarchical optical sensing layer 1 varies linearly with the normalised pressure. No hysteresis is observed by increasing and decreasing the pressure. Finally the signal variation is reproducible. On the contrary, the signal of a mesoporous film is not linearly dependant of the pressure, and after one cycle only, the emitted intensity is reduced ($I_{ref}/I>1$).

Figure 10A:
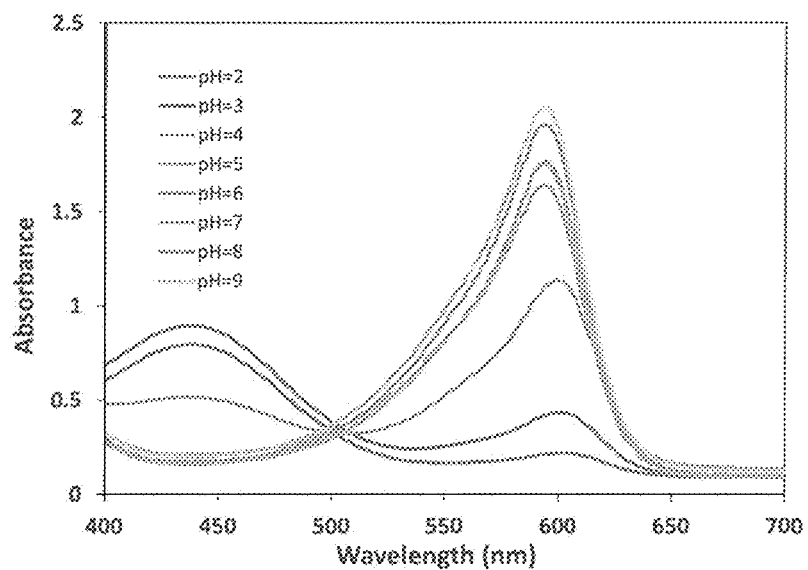
FIGS. 10A-10C—Optical spectra for a pH sensor incorporating an optical sensing layer according to the invention (FIG. 10A), an optical sensing layer based on a mesoporous layer (FIG. 10B) or on a microporous layer (FIG. 10C)
Figure 10B:
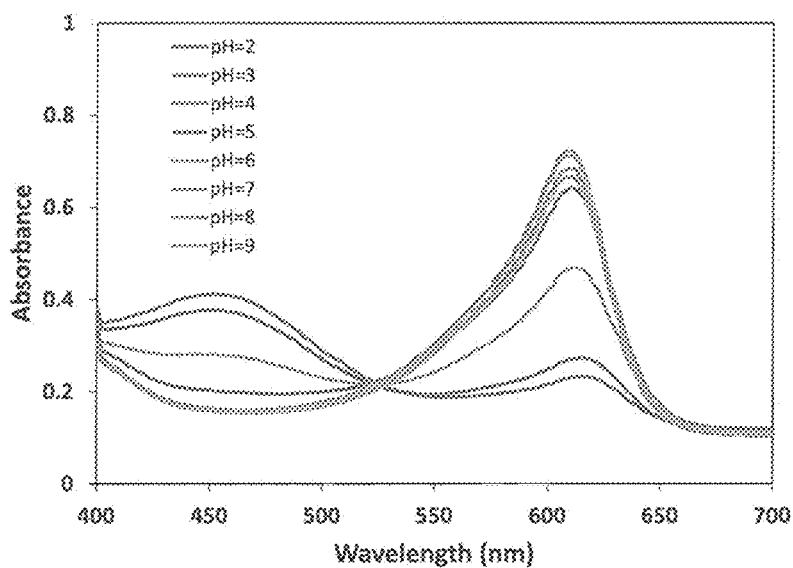
Figure 10:
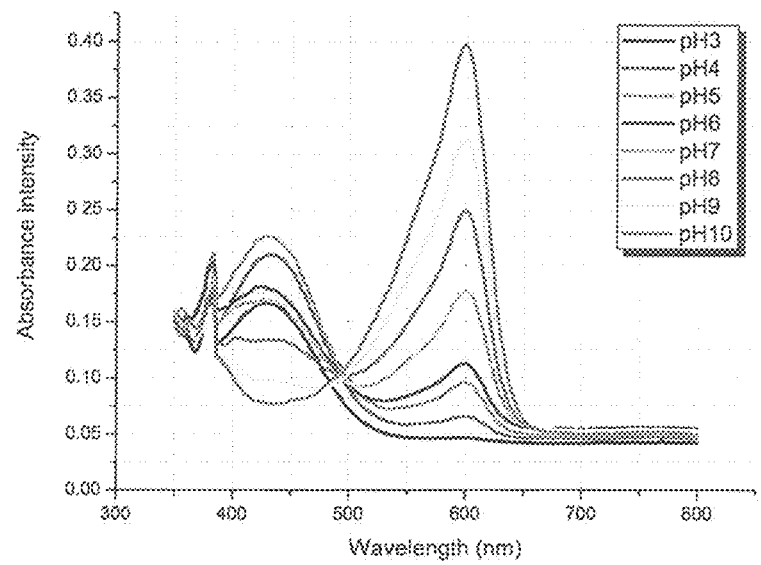

The gain in intensity with the hierarchical optical sensing layer of the invention over a microporous layer is illustrated by FIG. 10. A bromophenol blue functionalised microporous layer is 500 nm thick with an absorbance maximum around 0.4. This maximum is increased to 0.8 and 2 by inserting this microporous layer into a $SiO_2$ mesoporous film with a thickness of 12 μm and 40 μm respectively to form a hierarchical optical sensing layer according to the invention.

Figure 8:
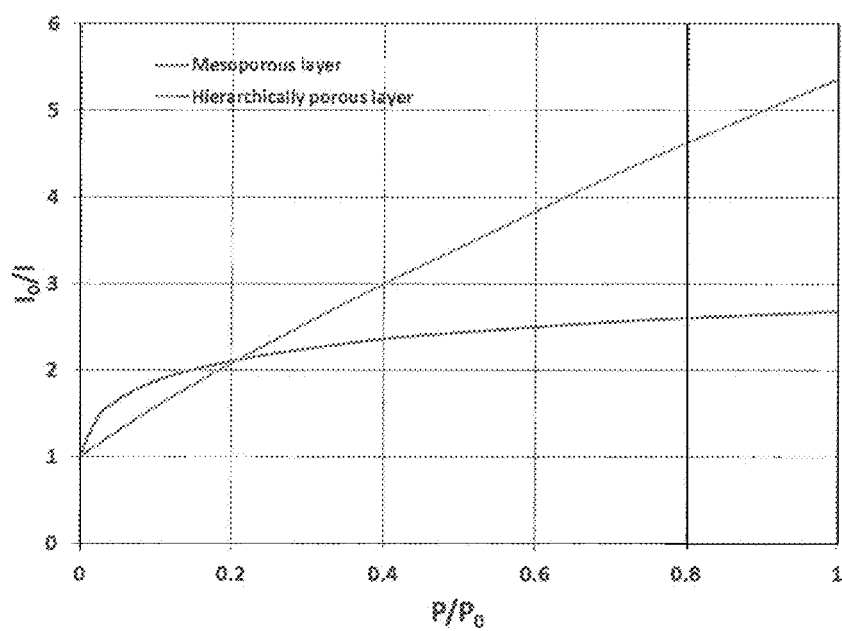
FIG. 8—a Stern-Volmer plot for oxygen sensing using an oxygen sensor incorporating an optical sensing layer according to the invention (Hierarchically porous film) and an optical sensing layer based on a purely mesoporous film.

Finally, FIG. 8 illustrates a Stern-Volmer plot for oxygen sensing in an alumina mesoporous matrix 5 with the above-mentioned indicator dye 9 and with a microporous matrix 7 (SG) or without (in $CH_2Cl_2$ solvent instead). The sol-gel microporous matrix is identical to the one described for FIG. 3. Both figures are representations of the variation of the emission intensity as a function of the normalised total pressure, therefore the normalised oxygen partial pressure (P=0 in pure $N_2$, $P=P_0$ at atmospheric pressure). The functionalised layers in $CH_2Cl_2$ dye solution exhibit two almost linear behaviours, one at low oxygen pressure ($P/P_0<0.05$) with a high sensitivity, and one at higher pressure ($P/P_0>0.3$) with a very low sensitivity.

In comparison, the sol-gel functionalised mesoporous supports according to the invention, exhibit a linear response over the whole pressure range. Then the final sensitivity is much higher than the one of the mesoporous matrix functionalised from a $CH_2Cl_2$ solution. The sensitivity performances of the hierarchical system remain stable for several weeks.

Example of Formulation for pH Sensing Films

A first example of producing an optical sensing layer for detecting pH, i.e. detecting the concentration of $H^+$ ions as a chemical species of interest follows hereunder.

In a typical experiment, 0.3 mL of (3-Glycidoxypropyl) methyldiethoxysilane and 3.44 mL of tetraethoxysilane are added to 4.1 mL of ethanol. Then 1.15 mL of HCl 1M is added dropwise. The pH indicator dye 9 (Bromocresol purple) is then added in a 2:1 molar ratio.

The resulting sol is then spread over mesoporous matrix 5, comprising silica or alumina. The thus functionalized mesoporous matrix 5 is dried overnight in room conditions, the sol drying on the surface of mesoporous matrix 5 to form microporous matrix 7 comprising the bromocresol purple indicator dye 9.

Figure 9A:
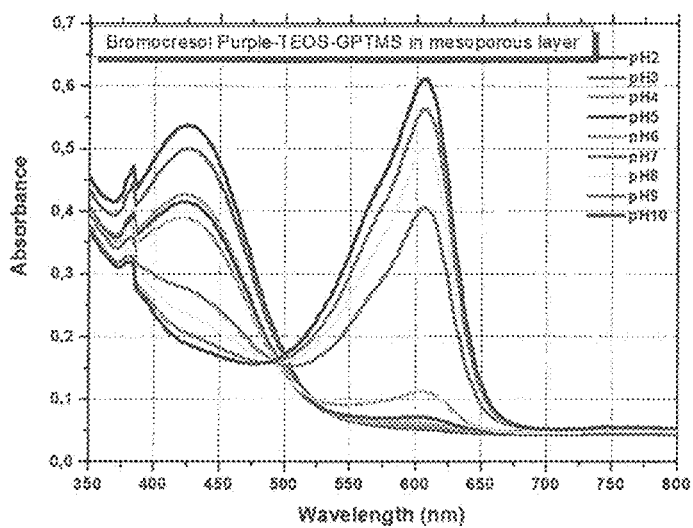
FIGS. 9A and 9B—a calibration curve for a pH sensor incorporating an optical sensing layer according to the invention.
Figure 9B:
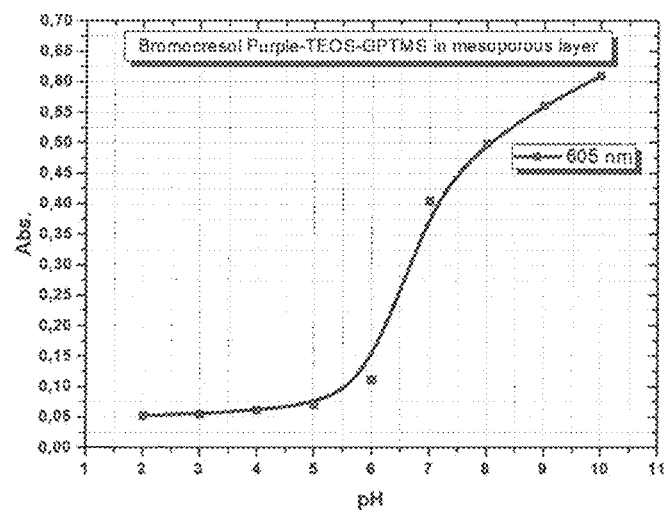

FIGS. 9A and B illustrate respectively the absorbance spectra obtained with the first example sensing layer and a representative calibration curve for bromocresol purple indicator dye 9, reporting the absorbance intensity at 605 nm of the functionalised layer as a function of pH. The sensitivity of the hierarchical functionalised layer is important in the 5-10 pH range.

A second example of producing a pH detecting optical sensing layer consists in mixing 0.71 mL of methyltriethoxysilane MTES and 0.68 mL of (3,3,3-trifluoropropyl) trimethoxysilane (FTP-TMOS) and 2.3 mL of ethanol. Then 0.77 mL of HCl acidified water (pH=1) is added dropwise. Finally, 7.1 mg of bromophenol blue is added to the sol. The resulting sol is blade coated onto a mesoporous silica layer. This film is then dried at room temperature for 2 hours, and cured by soaking into a pH=9 phosphate buffer solution overnight. The absorbance spectra obtained with this inventive sensing layer are reported in FIG. 10A.

As a comparison FIG. 10B represents the absorbance spectra obtained a from a prior art optical sensing layer consisting of a mesoporous silica layer with the same thickness as in the 10A example, but functionalised with an ethanolic solution of bromophenol blue with the same concentration as in the sol of the 10A example of the pH detecting sensor previously described. Likewise, FIG. 10C represents the absorbance spectra obtained from a prior art optical sensing layer consisting of a microporous sol containing bromophenol blue with the same concentration as in the sol of the second example spin-coated on a glass slide. From the comparison of the spectra shown in FIGS. 10B and 10C with the spectra of FIG. 10A, one can observe that the signal intensity measured either with a sensor comprising only a mesoporous layer (FIG. 10B) or only a microporous layer (FIG. 10C) is lower than the signal intensity of the spectra of FIG. 10A obtained with the optical sensing layer of the invention. Moreover, the stability in aqueous solutions for the mesoporous sensor is poor, the dye being able to leach out from the mesoporous layer. However, no leaching of the dye have been observed over 2 weeks when the dye is encapsulated into the silanes matrix (FIGS. 10A and 10C).

A third example is based on the immobilisation of a phenol red-tetraoctylammonium hydroxide pair in a hierarchical coating. A silicate sol is prepared by mixing 0.71 mL of methyltriethoxysilane MTES, 0.68 mL of FTP-TMOS, and 2.6 mL of ethanol. Then 0.5 mL of HCl acidified water (pH=1) is added dropwise. In parallel, 12 mg of phenol red was dissolved 3.03 mL of 20% methanolic solution of tetraoctylammonium hydroxide (TONOH) diluted with 1.97 mL of ethanol. A 50/50 volumic mixture of the sol and the solution was then blade coated onto a mesoporous silica layer. An equivalent volume of 20% methanolic solution of TONOH solution was then spread on the functionalised mesoporous layer. Finally, the functional film was cured overnight in a pH=9 phosphate buffer solution.

Figure 11:
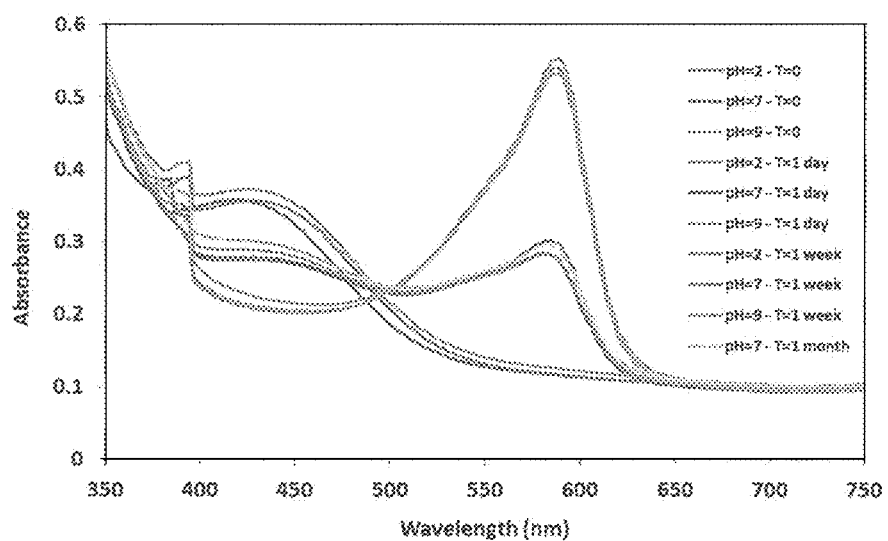
FIG. 11—Absorbance spectra of pH sensitive patches soaked in pH=2-7-9 solutions, just after the preparation (T=0), and aged in room conditions for 1 day, 1 week, or 1 month.

The spectra of the films soaked in pH=2-7-9 solutions for various durations up to 1 month are reported in FIG. 11. These results demonstrate the excellent stability of the films after 1 month in these aqueous solutions.

Example of Formulation for $CO_2$ Gas Sensing Films

In a typical experiment, 0.69 mL of MTES, 0.66 mL of FTP-TMOS are dissolved in 2.5 mL of ethanol. The mixture is hydrolysed with 0.5 mL of pH=1 water (HCl). In parallel, 100 mg of m-cresol purple are dissolved in 7.81 mL of 20% methanolic TONOH solution diluted with 2.19 mL of ethanol. After 2 hours stirring, both mixtures and 20% methanolic TONOH solution are mixed in a 1/1/1 volumic ratio. The final mixture is blade coated over a mesoporous layer. The functionalised layer is then thermally cured at 85° C. for 3 hours.

Figure 12:
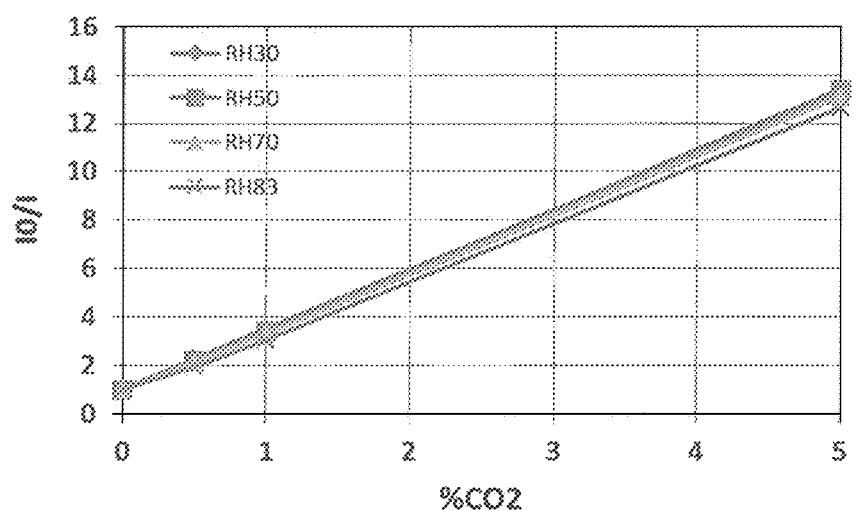
FIG. 12—Stern-Volmer plots for $CO_2$ sensing patches measured at different humidity levels.

The spectra are registered with a set-up at different $CO_2$ content (0-0.5-1-5%) and various humidity levels (30-50-70-83%). The Stern-Volmer plots for each humidity rate are obtained from the normalised variation of the 600 nm peak intensity (FIG. 12). One can therefore observe the extreme proximity of the plots at all tested humidity levels, the plots almost overlapping each other. This results show that hierarchical matrix sensors according to the invention containing a pH indicator is highly sensitive to $CO_2$ over the 0-5% range and not sensitive to humidity over the 30-85% range. Actually, the inventors have observed that the differences between the plots are of the same order as the measurement tolerances in the test set-up. This further confirms the independence of the optical sensing layers of the invention with respect to humidity.

The invention claimed is:

1. An optical sensing layer (1) for detecting a chemical species, said layer comprising:
   a substrate (3);
   a mesoporous matrix (5) disposed on the substrate;
   a microporous matrix (7) disposed within the mesoporous matrix, the microporous matrix (7) comprising an indicator dye (9) dispersed therein, said indicator dye (9) exhibiting changes in optical properties in response to the presence of said chemical species, wherein, the mesoporous matrix (5) is a layer having a thickness of 1-50 µm, the mesoporous matrix (5) comprising pore of diameters in the range of between 10 nm and 50 nm, the microporous matrix (7) is a layer having a thickness of less than 100 nm, the microporous matrix (7) comprising pore of diameters of less than 2 nm, and the pores of the mesoporous matrix are coated with the microporous matrix disposed within the mesoporous matrix.

2. The optical sensing layer (1) according to claim 1, wherein the mesoporous matrix comprises a film of mesoporous inorganic materials of nanoparticles dispersions of an oxide.

3. The optical sensing layer (1) according to claim 2, wherein the film of mesoporous inorganic materials of the mesoporous matrix comprises nanoparticles dispersions of silica or alumina.

4. The optical sensing layer (1) according to claim 1, wherein the microporous matrix is a siloxane network.

5. The optical sensing layer (1) according to claim 1, wherein the indicator dye comprises at least one of the following dye molecules: bromophenol blue, alizarin, methyl red, phenol red, m-cresol purple, p-xylenol blue, naphtol blue black, fluorescein, eosin, calmagite, naphtholphtalein, ruthenium complexes, porphyrines, and pyrenes.

6. The optical sensing layer according to claim 1, wherein said mesoporous matrix is formed as a layer having a thickness of 5-40 µm.

7. A sensor system (10) comprising:
(1) an optical sensing layer (1) according to claim 1;
(2) a light source (11) arranged to illuminate said microporous matrix (7) and said indicator dye (9);
(3) a detector (13) arranged to receive light emanating from said indicator dye (9).

8. A method of producing an optical sensing layer (1) comprising the steps of:
providing a substrate (3);
depositing a mesoporous matrix (5) on the substrate;
subsequent to said step of depositing a mesoporous matrix (5) on the substrate, depositing a microporous matrix (7) within the mesoporous matrix (5), the microporous matrix (7) comprising an indicator dye (9) dispersed therein, said indicator dye (9) exhibiting changes in optical properties in response to the presence of said chemical species, wherein, the mesoporous matrix (5) is deposited as a layer having a thickness of 1-50 µm, and the mesoporous matrix (5) having pores with diameters in the range of between 10 nm and 50 nm, the microporous matrix (7) is deposited as a layer having a thickness of less than 100 nm, the microporous matrix (7) comprising pore of diameters of less than 2 nm, and the pores of the mesoporous matrix are coated with the microporous matrix disposed within the mesoporous matrix.

9. The method according to claim 8, wherein the mesoporous matrix comprises a film of mesoporous inorganic materials obtained by deposition of nanoparticles dispersions of an oxide.

10. The method according to claim 9, wherein the mesoporous matrix comprises a film of mesoporous inorganic materials obtained by deposition of nanoparticles dispersions of silica or alumina.

11. The method according to claim 8, wherein the microporous matrix is a siloxane network obtained by hydrolysis and condensation of a silane mixture.

12. The method according to claim 11, wherein the microporous matrix is obtained from a sol composed of a solvent, a mixture of silanes and acidified water.

13. The method according to claim 8, wherein the mesoporous matrix is deposited such that the mesoporous matrix exhibits pore diameters in the range of between 10 and 50 nm.

14. The method according to claim 8, wherein the indicator dye comprises at least one of the following dye molecules: bromophenol blue, alizarin, methyl red, phenol red, m-cresol purple, p-xylenol blue, naphtol blue black, fluorescein, eosin, calmagite, naphtholphtalein, ruthenium complexes, porphyrines, and pyrenes.

15. The method according to claim 8, wherein said mesoporous matrix is deposited as a layer having a thickness of 5-40 µm.

* * * * *